US010563886B2

(12) United States Patent
McCormick et al.

(10) Patent No.: US 10,563,886 B2
(45) Date of Patent: Feb. 18, 2020

(54) AIR QUALITY SENSOR AND DATA ACQUISITION APPARATUS

(71) Applicant: Grand Valley State University, Allendale, MI (US)

(72) Inventors: Leo M. McCormick, Grand Rapids, MI (US); Sean M. McManus, Allendale, MI (US); Tom Michalak, Grand Rapids, MI (US)

(73) Assignee: Grand Valley State University, Allendale, MI (US)

( * ) Notice: Subject to any disclaimer, the term of this patent is extended or adjusted under 35 U.S.C. 154(b) by 150 days.

(21) Appl. No.: 15/819,632

(22) Filed: Nov. 21, 2017

(65) Prior Publication Data
US 2018/0363939 A1 Dec. 20, 2018

Related U.S. Application Data

(63) Continuation of application No. 62/522,159, filed on Jun. 20, 2017.

(51) Int. Cl.
| | |
|---|---|
| *G01N 7/00* | (2006.01) |
| *F24F 11/89* | (2018.01) |
| *G01N 1/22* | (2006.01) |
| *G01N 1/26* | (2006.01) |
| *F24F 11/74* | (2018.01) |
| *F24F 110/70* | (2018.01) |

(Continued)

(52) U.S. Cl.
CPC .............. *F24F 11/89* (2018.01); *F24F 11/74* (2018.01); *G01N 1/2273* (2013.01); *G01N 1/26* (2013.01); *F24F 2110/50* (2018.01); *F24F 2110/70* (2018.01); *G01N 33/004* (2013.01)

(58) Field of Classification Search
CPC ........ F24F 11/89; F24F 11/74; F24F 2110/50; F24F 2110/70; D01N 1/2273; D01N 1/26
USPC .......................................................... 422/83
See application file for complete search history.

(56) References Cited

U.S. PATENT DOCUMENTS

| | | | |
|---|---|---|---|
| 5,184,501 A * | 2/1993 | Lewis ................. | G01N 1/2252 73/23.31 |
| 5,292,280 A * | 3/1994 | Janu ......................... | F24F 7/08 454/229 |
| 5,293,771 A | 3/1994 | Ridenour | |

(Continued)

OTHER PUBLICATIONS

Search Report and Written Opinion of the International Searching Authority, International Application No. PCT/US18/35937, dated Aug. 30, 2018 (11 pages).

*Primary Examiner* — Helena Kosanovic
(74) *Attorney, Agent, or Firm* — Price Heneveld LLP (57) ABSTRACT

An air sampling system configured to detect an air quality metric for a plurality of volumetric regions is disclosed. The system comprises an air sample return unit, an air flow controller, and at least one sensor. The air sample return unit is configured to independently transfer air from the plurality of regions as a plurality of air samples. The air flow controller is configured to receive each of the plurality of air samples and selectively direct a selected sample to a sensor supply line and the remainder of the samples to a sample purge line. The at least one sensor is configured to measure an air quality metric of the selected sample and communicate the air quality metric to a controller. The remainder of the air samples are directed to the air sample return unit throughout operation.

19 Claims, 4 Drawing Sheets

(51) Int. Cl.
   *G01N 33/00*      (2006.01)
   *F24F 110/50*     (2018.01)

(56) References Cited

U.S. PATENT DOCUMENTS

| | | |
|---|---|---|
| 5,357,781 A    | 10/1994 | Tikijian |
| 5,394,934 A    | 3/1995  | Rein et al. |
| 5,464,369 A    | 11/1995 | Federspiel |
| 5,550,752 A    | 8/1996  | Federspiel |
| 5,976,010 A    | 11/1999 | Reese et al. |
| 6,125,710 A    | 10/2000 | Sharp |
| 6,241,950 B1   | 6/2001  | Veelenturf et al. |
| 6,425,297 B1   | 7/2002  | Sharp |
| 7,302,313 B2   | 11/2007 | Sharp et al. |
| 7,389,158 B2   | 6/2008  | Desrochers et al. |
| 7,434,413 B2   | 10/2008 | Wruck |
| 8,066,558 B2   | 11/2011 | Thomle et al. |
| 8,147,302 B2   | 4/2012  | Desrochers et al. |
| 9,109,981 B2   | 8/2015  | Sharp |
| 2013/0260668 A1 | 10/2013 | Stakutis et al. |
| 2015/0253165 A1 | 9/2015  | Ajay et al. |
| 2015/0323427 A1 | 11/2015 | Sharp |

\* cited by examiner

AIR QUALITY SENSOR AND DATA ACQUISITION APPARATUS

CROSS-REFERENCE TO RELATED APPLICATION

This application claims priority to and the benefit under 35 U.S.C. § 119(e) of U.S. Provisional Patent Application No. 62/522,159, filed on Jun. 20, 2017, entitled "AIR QUALITY SENSOR AND DATA ACQUISITION APPARATUS," the entire disclosure of which is hereby incorporated herein by reference.

TECHNOLOGICAL FIELD

The present disclosure generally relates to air monitoring systems and, more particularly, relates to air monitoring systems utilizing multipoint air sampling.

BACKGROUND OF THE DISCLOSURE

Building air supply and control systems are becoming increasingly important due to increases in energy cost. In various building ventilation systems (e.g. HVAC systems), it may be beneficial to improve data acquisition for each room of the building. The disclosure provides for a variety of improvements in air sampling and air quality control for building ventilation and control systems.

BRIEF SUMMARY

According to one aspect of the present disclosure, an air sampling system configured to detect an air quality metric for a plurality of volumetric regions is disclosed. The system comprises an air sample return unit, an air flow controller, and at least one sensor. The air sample return unit is configured to independently transfer air from the plurality of regions as a plurality of air samples. The air flow controller is configured to receive each of the plurality of air samples and selectively direct a selected sample to a sensor supply line and the remainder of the samples to a sample purge line. The at least one sensor is configured to measure an air quality metric of the selected sample and communicate the air quality metric to a controller. The air sample return unit and the remainder of the air samples are directed to the air sample return unit throughout operation.

According to another aspect of the present disclosure, an air sampling system is disclosed. The system is configured to detect an air quality metric for a plurality of regions. The system comprises an air sample unit and an air flow controller. The air sample unit is disposed in an air flow generated by an air supply unit of an HVAC system and is configured to generate a suction with energy derived from the air flow. The air flow controller is configured to selectively transfer air from the plurality of regions via the suction as a plurality of air samples. The system further comprises at least one sensor in fluid communication with the air flow controller. The at least one sensor is configured to measure an air quality metric of a selected sample of the plurality of air samples and communicate the air quality metric to a controller. The selected sample and a remainder of the plurality of air samples are concurrently drawn to the air sample unit via the suction.

According to yet another aspect of the present disclosure, a method for detecting air quality for a plurality of volumetric regions of a building is disclosed. The method comprises receiving an air flow generated by an air supply unit and generating a suction in a suction line with energy derived from the air flow. The method further comprises drawing room air samples from a plurality of rooms with the suction and selectively directing at least one selected room air sample to a sensor device while directing a remainder of the room air samples to the suction line bypassing the at least one sensor. The method additionally comprises detecting an air quality metric of the at least one selected room air sample and changing the at least one selected room air sample over time among the plurality of room samples such that the air quality metric is identified for the plurality of rooms.

These and other aspects, objects, and features of the present disclosure will be understood and appreciated by those skilled in the art upon studying the following specification, claims, and appended drawings. It will also be understood that features of each embodiment disclosed herein may be used in conjunction with, or as a replacement for, features of the other embodiments.

DETAILED DESCRIPTION OF EMBODIMENTS

The present illustrated embodiments reside primarily in combinations of method steps and apparatus components related to an electro-optic device. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Modern heating, ventilation, and air conditioning (HVAC) systems may provide for independent control of various regions or rooms within a building. In this way, climate control and air quality may be monitored and controlled for each region or room. In addition to the benefits of improved comfort and air quality, systems may also be configured to reduce energy consumption. In some cases, conserving energy may include determining occupancy of each room or region. In response to the occupancy or level of occupancy, the HVAC setting may be optimized to ensure that the air quality is maintained. However, there are a variety of challenges that may be associated with implementing such systems on a large scale while maintaining economical HVAC control solutions. The following detailed description provides for a system and control method for an air sampling system that is both effective and economical.

Figure 1:
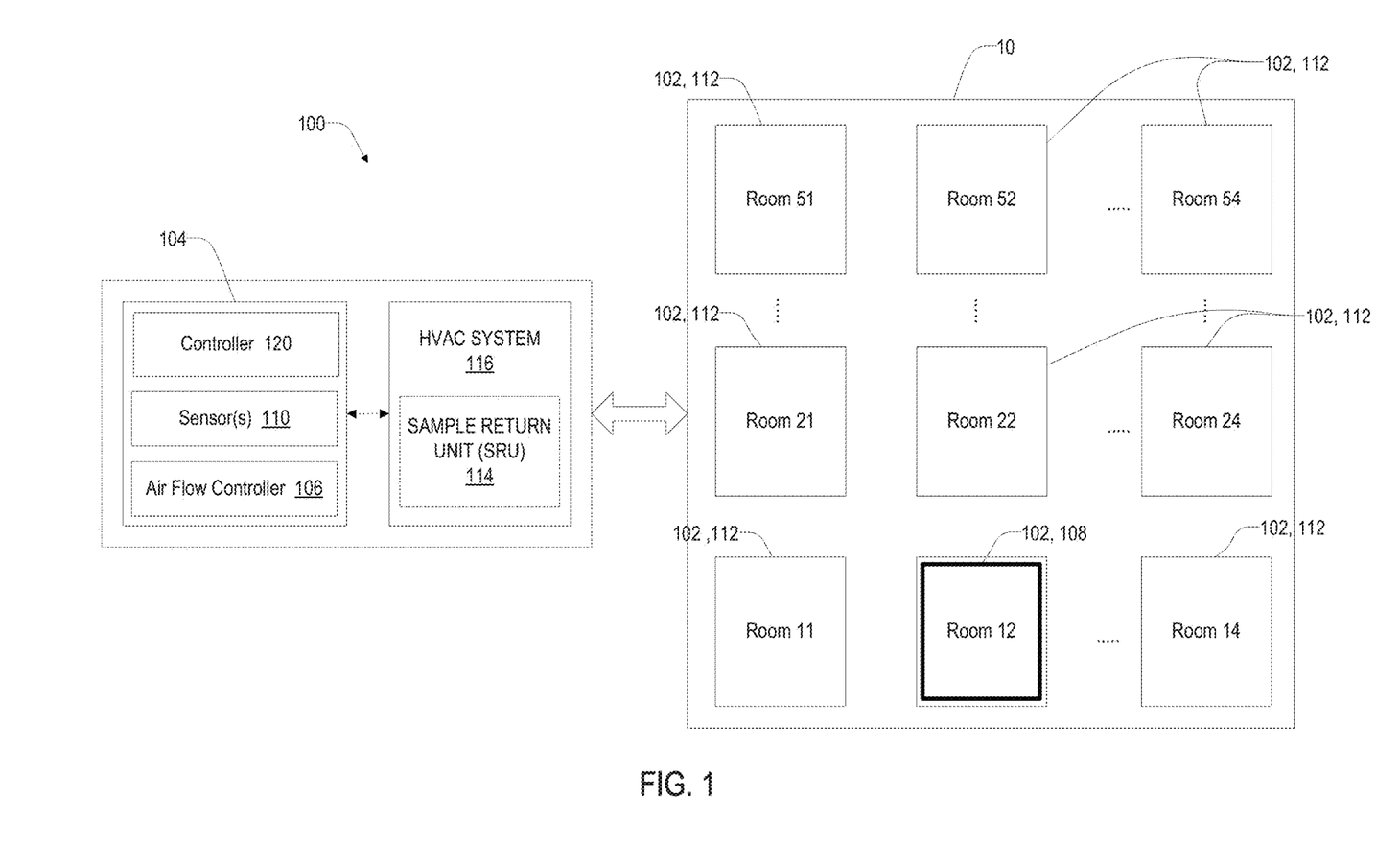
FIG. 1 is a block diagram of a building demonstrating a plurality of rooms incorporating an air sampling system.
Figure 2:
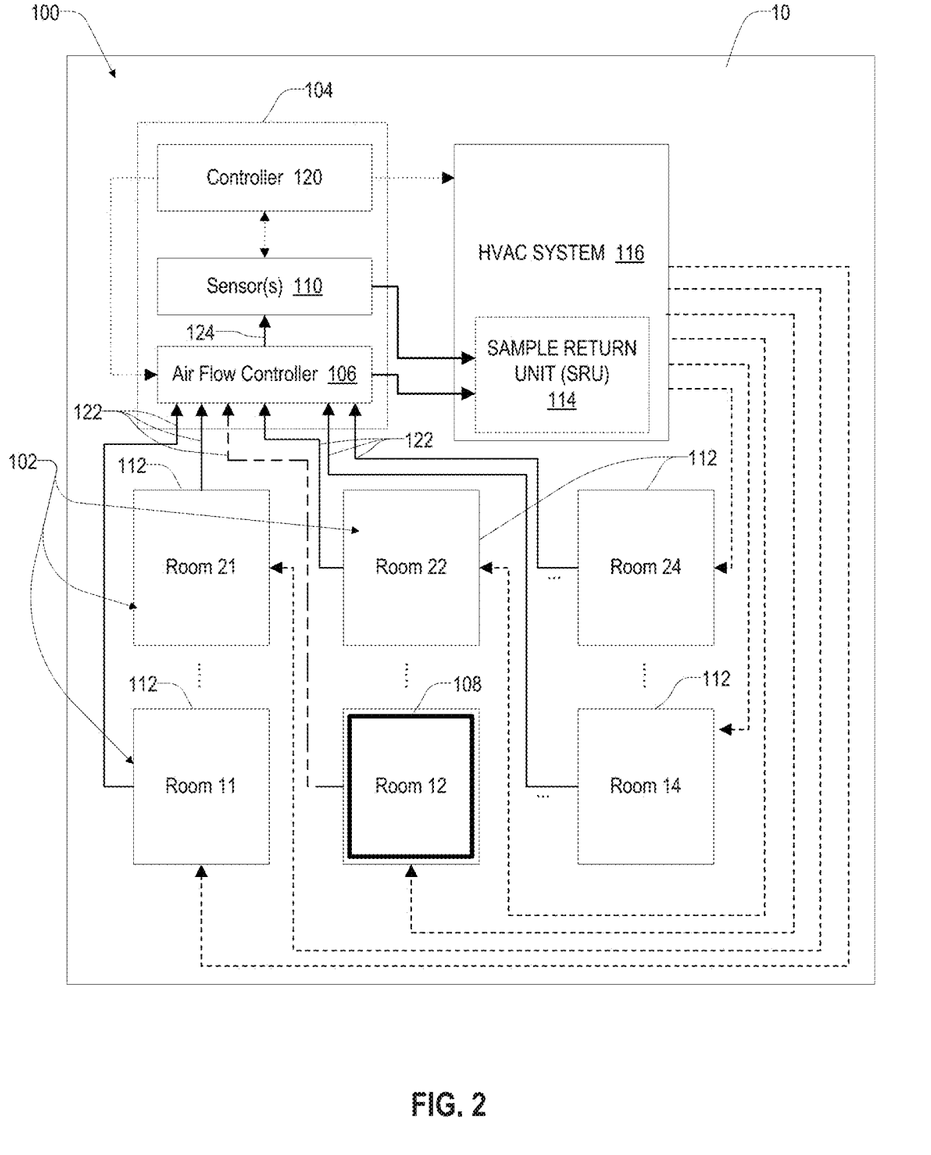
FIG. 2 is a block diagram of a building having an air sampling system.

Referring to FIGS. 1 and 2, block diagrams of a building 10 having an air sampling system 100 is shown. The air sampling system 100 may be configured to selectively measure at least one air quality characteristic from a plurality of areas of the building 10. For example, the system 100 may be configured to monitor various volumetric regions of a single room and/or monitor the conditions of each of a plurality of rooms 102 (e.g. rooms 11-14, 21-24, 51-54, etc.). The plurality of rooms 102 or areas of the building 10 may correspond to regions or volumetric spaces within a commercial building, residential building, multi-purpose building, etc. The disclosure may provide for various novel aspects configured to limit the installation and operating cost of the system 100, and may also provide for improved operational performance.

In an exemplary embodiment, the system 100 may comprise an air sampling device 104. The air sampling device 104 may correspond to a scalable monitoring device configured to sample the air from each of the plurality of rooms 102 via an air flow controller 106. The air flow controller 106 may comprise a header configured to receive multiple inputs corresponding to each of the plurality of rooms 102. The air flow controller 106 may be configured to selectively direct a room air sample from a selected room 108 (e.g. room 12) to one or more sensors 110. While drawing the room air sample from the selected room 108, the air sampling device 104 may be configured to draw air from the idle rooms 112 of the plurality of rooms 102. In this configuration, the sampling device may be operable to monitor a condition of the air in each of the plurality of rooms 102 with only limited and consistent delay to gather a current air sample. As will be discussed further herein, the delay of the air sampling device 104 to update a sample for each selected room may be consistent regardless of a distance of the selected room 108 from the sensor 110 of the sampling device 104.

The system 100 may further comprise an air transport motivator or sample return unit 114. The sample return unit 114 may correspond to an energy efficient air transport unit configured to function without a need for direct electrical power. In such embodiments, the sample return unit 114 may be configured to generate suction to draw the room air samples from each of the plurality of rooms 102 via a bulk supply fan of an existing heating, ventilation, and air conditioning (HVAC) system 116 of the building 10. For example, the sample return unit 114 may correspond to a Venturi Vacuum device configured to utilize differential pressure derived from the bulk supply fan of the HVAC system 116. Further details of the sample return unit 114 are discussed in reference to FIG. 3. The HVAC system 116 may be configured to provide heating, ventilation, and air conditioning to each of the rooms 102. In this configuration, the sampling return unit 114 may be configured to function without a direct supply of electrical energy.

Though the sample return unit 114 is described in the exemplary embodiment as a Venturi Vacuum device, in some embodiments, the sample return unit 114 may recover the room air samples utilizing conventional vacuum pumps or fans. For example, in some embodiments, the sample return unit 114 may utilize suction created via a reciprocating pump, screw or turbine compressor, or various devices configured to displace air in response to receiving electrical current. Such devices may be utilized to provide vacuum pressure to return the room air samples. However, these devices may be noisy, inefficient, and require more maintenance than the Venturi Vacuum device disclosed herein.

In the exemplary embodiment utilizing the Venturi Vacuum device, the only energy usage of the sample return unit 114 may be a small parasitic energy drawn from the bulk supply fan of the HVAC system 116. For example, the bulk supply fan may consume a small and potentially negligible increased power due to the energy usage of the sample return unit 114. The change in power usage may particularly be negligible when the air sampling system 100 is implemented in large buildings having multiple rooms and high volume HVAC systems 116. In this way, the air sampling system 100 may improve efficiency while limiting components and related maintenance that may be required when utilizing active devices to provide vacuum pressure to return the room air samples. As disclosed, the sample return unit 114 may utilize the existing fluid pressure from the HVAC system 116 to power the sample return unit 114 via the Venturi effect to improve efficiency and limit maintenance.

In operation, the sample return unit 114 may draw room air samples from each of the plurality of rooms 102 perpetually during operation of the bulk supply fan of the HVAC system 116. For example, the controller 120 of the air sampling system 100 may be configured to control the air flow controller 106 to direct a room air sample of a selected room 108 to a quality sensor of the at least one sensor 110 to measure a condition or quality parameter of the selected room 108. The quality sensor is identified as element 140 in FIG. 3 and is discussed further in reference to FIG. 3. Additionally, the air flow controller 106 may be configured to retrieve and purge room air samples 132 from each of the idle rooms 112 (e.g. rooms 11, 13, 14, and 21-24).

By continuously drawing the room air samples from each of the idle rooms 112 and the selected room 108, the air sampling system 100 may continuously supply updated air samples to the air flow controller 106. In this way, the system 100 may supply air samples from each of the rooms 102 to a central location of the air flow controller 106 and selectively direct the air sample from the selected room 108 to the quality sensor 140. Accordingly, the system 100 may avoid delays in updating the air samples from each of the idle rooms 112 that may otherwise be required to purge an associated length of the supply line 122 from each of the rooms 102 to the air flow controller 106. By continuously supplying updated air samples from each of the rooms 102 containing air that is representative of a current air quality, the sampling system 100 is operable to test each of the rooms 102 without significant delay that may otherwise be required to purge air samples. Accordingly, the air supplied from the air flow controller 106 to the at least one sensor 110 may only need to be purged from the air in the sensor supply line 124 rather than each of the air sample supply lines 122 when changing the selected room 108 among the plurality of rooms 102.

In operation, the controller 120 may measure the air quality of one or more of the rooms 102 by cycling the selected room 108 to supply an air sample from one or more of the rooms 102. For example, during such an operation, the controller 120 may control the air flow controller 106 and the at least one sensor 110 to measure the air quality of room 12. Following the measurement of the air quality in room 12, the controller 120 may generate a control signal configured to change the air flow controller 106 to select room 22 as the selected room 108. In this configuration, the idle rooms 112 may include rooms 11-14, 21, 23, and 24; the air samples from these rooms may be purged while the selected room 108 is designated as room 22.

The room air sample from room 22 may be directed by the air flow controller 106 such that the air entering the at least one sensor 110 is from room 22. The controller 120 may then allow a predetermined period of time for the room air sample from room 12 to purge from a sensor supply line 124 and to allow time for a change in the sampled air to become stable in the sensor 110. Once the predetermined period of time has lapsed, the controller 120 may monitor the at least one sensor 110 to identify a condition or quality parameter of the room air sample for room 22. If the room air samples from each of the rooms 102 were not delivered to the air flow controller 106 throughout operation, the purge time may increase dramatically and vary for each of the rooms 102 due to variations in the lengths of the air sample supply lines 122. Such variations and increases in purge time may result in delayed correction of air quality in each of the rooms 102 as well as increased maintenance and operational cost for the sampling system 100.

The controller 120 of the air sampling system 100 may continue to control the air flow controller 106 to test the condition or an air quality parameter of each of the rooms 102 in any sequence. The controller 120 may be configured to monitor each of the room air samples for each of the rooms 102 for a monitoring period, which may be independently specified for one or more of the rooms 102. Additionally, the air sampling system 100 may be configured to monitor the rooms 102 sequentially or in any order. For example, the controller 120 may be configured to control the air flow controller 106 to monitor a frequently occupied room with a greater frequency than other rooms of the plurality of rooms 102.

As discussed previously, the continuous delivery of the room air samples for each of the rooms 102 by the air flow controller 106 may limit a purging time required to gather a current or updated sample from the selected room 108. Additionally, the continuous delivery of the room air samples may limit a flow rate necessary for the sample return unit 114. In this way, the air sampling system 100 can maintain a low cycle time allowing the controller 120 to monitor the condition or an air quality parameter of each of the rooms 102 over a limited cycle time. The cycle time may correspond to a time required for the controller 120 to measure the condition or an air quality parameter of each of the rooms 102 and may also be referred to as a refresh rate.

Systems that do not utilize continuous delivery of the room air samples may require a significant increase in cycle time to monitor the rooms 102 or an increased flow rate for an air sample return unit. For example, the cycle time may increase due to increased purge time required to receive air sample data representative of the current air quality for a selected room 108. The flow rate of the air samples recovered from each room may be increased to limit the purge time, but such operation may require an air sample return device having increased power consumption, which may reduce operational efficiency and increase the noise of operation. Accordingly, the systems and methods disclosed provide for the air sampling system 100 to operate with improved efficiency while maintaining a responsive system having a short cycle time.

Figure 3:
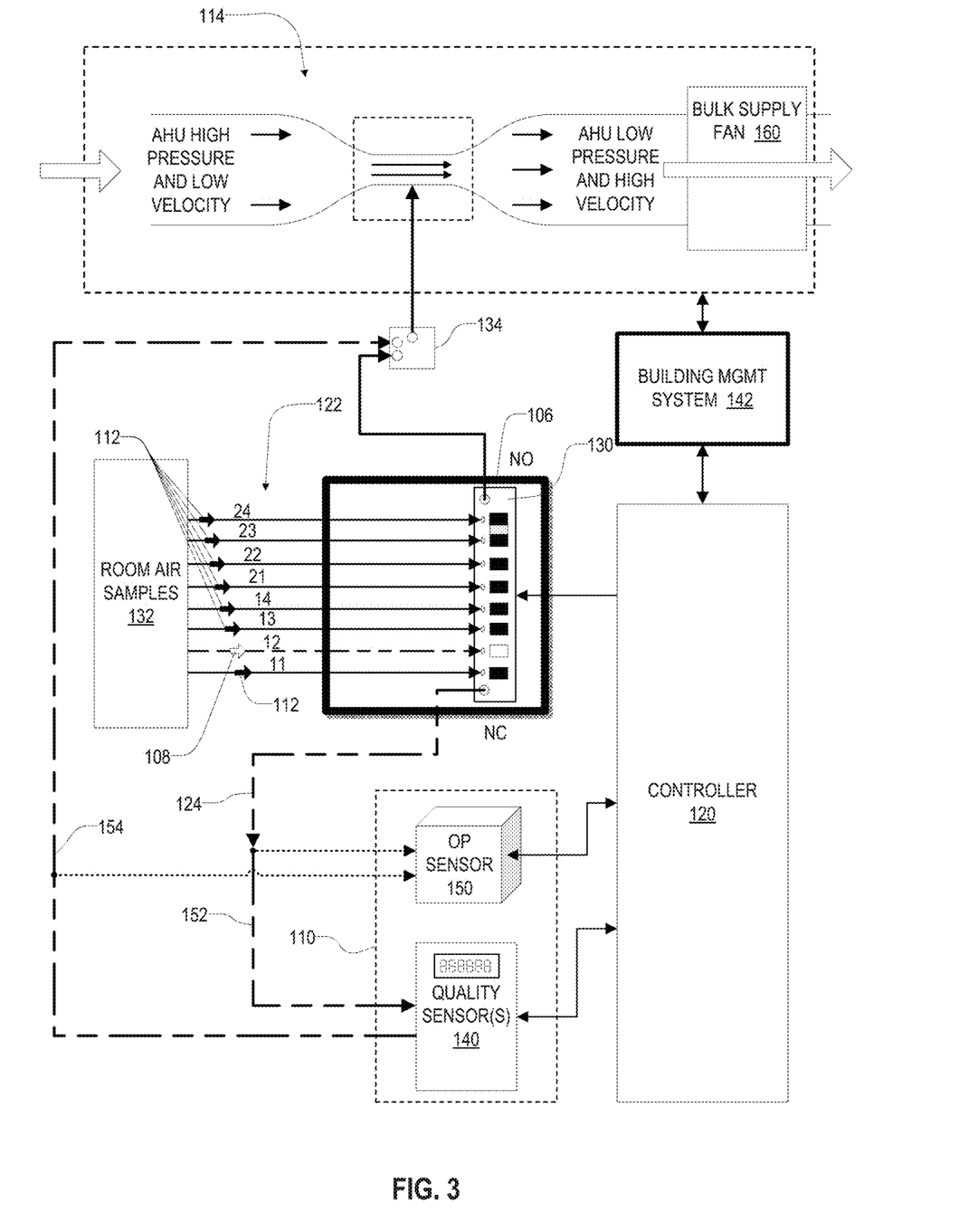
FIG. 3 is a schematic diagram of the air sampling system.

Referring now to FIG. 3, a schematic diagram of the air sampling system 100 is shown. As illustrated in FIG. 3, the air flow controller 106, the at least one sensor 110, and the sample return unit 114 are demonstrated in further detail. The air flow controller 106 may comprise a multi-input header 130 configured to receive each of a plurality of room air samples 132 from the plurality of rooms 102. The controller 120 may be configured to output a control signal to control the air flow controller 106 identifying a room of the plurality of rooms 102 to be measured for an air quality parameter or air condition. In response to receiving the signal, the air flow controller 106 may control one or more valves to direct the room air sample from the selected room 108 to the at least one sensor 110. In this way, the room air sample from the selected room 108 may be directed to the at least one sensor 110.

During operation, the room air samples 132 from each of the plurality of rooms 102 may be consistently delivered to the air flow controller 106 via the air sample supply lines 122, each of which is in fluid communication with the air in one of the plurality of rooms 102. The room air samples 132 may be delivered at a rate of a volumetric displacement of air induced by a pressure differential generated in the sample return unit 114. The room air sample from the selected room 108 may be delivered to the at least one sensor 110. From the at least one sensor 110, the air may be drawn into the sample return unit 114 via a coupler 134. Concurrently to the delivery of the room air sample from the selected room 108, the room air samples from the idle rooms 112 may be drawn through the air flow controller 106 to the sample return unit 114 via the coupler 134. In this configuration, the room air samples 132 from each of the plurality of rooms 102 may be consistently delivered to the air flow controller 106 to provide updated room air samples for each of the plurality of rooms 102 throughout operation.

The at least one sensor 110 may correspond to a variety of types of sensors configured to measure one or more properties or air quality parameters of the room air samples 132. In some embodiments, the at least one sensor 110 may correspond to one or more air quality sensors 140 configured to detect a condition or change in condition in each of the room air samples 132. The air quality sensor 140 may be configured to communicate one or more measurements or other data to the controller 120. The controller 120 may process the one or more measurements or other data to identify air quality conditions or metrics for each of the plurality of rooms 102.

The measurements communicated to the controller 120 may be utilized to determine an appropriate action to improve the air quality for a specific room of the plurality of rooms 102. In this way, the controller 120 may identify a condition or change in condition in one or more air quality parameters. Based on the identified condition or change, the controller 120 may communicate a ventilation control signal configured to induce a building management system (BMS) 142 to take corrective action. In response to the ventilation control signal, the BMS 142 may control the HVAC system 116 to provide ventilation, heat, and/or cooled air to a specific room or group of rooms of the plurality of rooms 102.

In an exemplary embodiment, the quality sensor 140 may correspond to a carbon dioxide ($CO_2$) sensor. The $CO_2$ sensor may be configured to measure a $CO_2$ level of the air in the selected room 108. In such an embodiment, the quality sensor 140 (e.g. the $CO_2$ sensor) may be configured to communicate the $CO_2$ level of the selected room 108 to the controller 120. Based on a change or measurement of the $CO_2$ level, the controller 120 may communicate a ventilation control signal to the BMS 142. Based on the ventilation control signal, the BMS 142 may control the HVAC system 116 to provide ventilation, heating, or cooling to the selected room 108 (e.g. room 12). In this way, the system 100 may be configured to monitor the air quality of each of the rooms 102 and communicate the $CO_2$ level to the building management system 142. Accordingly, the system 100 may be utilized to determine if the ventilation supplied by the HVAC system 116 is sufficient to control the $CO_2$ level in each of the rooms and communicate the $CO_2$ level or a representative control signal to the building management system 142 such that the $CO_2$ level in each of the rooms 102 may be maintained by the building management system 142 within a desired operating range.

Throughout operation, the controller 120 may continue to inspect the room air samples from each of the rooms 102 by controlling the air flow controller 106 to cycle each of the plurality of rooms 102 as the selected room 108. For example, after the controller 120 has received the air quality parameter or measurement from the quality sensor 140 for a first room (e.g. room 12), the controller 120 may output a signal configured to control the air flow controller 106 to deliver a room air sample from a second room (e.g. room 22) to the quality sensor 140. The room air sample for the second room (e.g. room 22) may be measured by the quality sensor 140, which may communicate an air quality parameter to the controller 120. Based on the air quality parameter from the second room (e.g. room 22), the controller 120 may communicate a ventilation control signal to the building management system 142. In response to the ventilation control signal, the building management system 142 may control a ventilation, heating, and/or cooling property of the air supplied to the second room (e.g. room 22). In this way, the air sampling device 104 may provide control information and/or measurement information configured to identify an air quality parameter of the each of the plurality of rooms 102.

Though discussed in reference to the $CO_2$ sensor, the air quality sensor 140 may correspond to any form of device configured to measure a condition or an air quality parameter of an air sample. For example, the air quality sensor 140 may correspond to one or more forms of volatile organic compound (VOC) sensors, humidity sensors, $CO_2$ sensors, carbon monoxide (CO) sensors, ozone sensors, etc. Accordingly, the air sampling device 104 may be configured to provide various forms of air quality information to the building management system 142. In various embodiments, the controller 120 of the air sampling device 104 may be configured to provide various signals, measurements, and/or control instructions to the building management system 142 to suit a particular application of the air sampling system 100.

The at least one sensor 110 of the system 100 may further comprise an operation sensor 150, which may correspond to a differential pressure transmitter or pressure sensor. The operation sensor 150 may be connected to an inlet line 152 and an outlet line 154 of the quality sensor 140. In this configuration, the operation sensor 150 may be configured to identify if the air flow provided to the quality sensor 140 is sufficient to measure the air quality parameter of the selected room 108. Additionally, the operation sensor 150 may be configured to identify a change in pressure over the operating life or maintenance cycle of the air sampling system 100. For example, the controller 120 may monitor pressure data supplied by the operation sensor 150 to identify a change in pressure over time or a pressure below a predetermined threshold. Such changes in operating pressure may be utilized by the controller 120 to identify a maintenance condition or failure in operation of the air sampling device 104.

Still referring to FIG. 3, the sample return unit 114 may correspond to an air transport motivator. The sample return unit 114 may correspond to an energy efficient air transport unit configured to function without a need for direct electrical power or a dedicated mechanical drive, vacuum or propulsion system. In such embodiments, the sample return unit 114 may be configured to generate suction to draw the room air samples 132 from each of the plurality of rooms 102 in response to by being positioned within an air flow of a bulk supply fan 160 or air displacement device of the HVAC system 116. For example, the sample return unit 114 may correspond to a Venturi Vacuum device configured to utilize differential pressure from the air flow in the form of a vacuum pump 162 derived from the bulk supply fan 160. The HVAC system 116 may be configured to provide heating, ventilation, and/or air conditioning to each of the rooms 102. In this configuration, the air sampling system 100 may be configured to function without a dedicated or air displacement device requiring energy that is not already utilized by operating the HVAC system 116.

Though the sample return unit 114 is described in the exemplary embodiment as a Venturi Vacuum device, in some embodiments, the sample return unit 114 may recover the room air samples utilizing conventional vacuum pumps or fans. For example, in some embodiments, the sample return unit 114 may utilize suction created via a reciprocating pump, screw or turbine compressor, or various devices configured to displace air in response to receiving electrical current. Such devices may be utilized to provide vacuum pressure to return the room air samples. However, these devices may be noisy, inefficient, and require more maintenance than the Venturi Vacuum device disclosed herein.

As discussed herein, in the exemplary embodiment, the only energy usage of the sample return unit 114 may be a small parasitic energy drawn from the bulk supply fan 160 of the HVAC system 116. For example, the bulk supply fan 160 may consume a small and potentially negligible increase in power to provide the suction necessary to operate the sample return unit 114. In this way, the air sampling system 100 may improve efficiency while limiting components and related maintenance that may be required when utilizing active devices to provide vacuum pressure to return the room air samples. Instead, the sample return unit 114 may utilize the existing fluid pressure from the HVAC system 116 to generate suction to power the sample return unit 114 via the Venturi effect to improve efficiency and limit maintenance.

In operation, the sample return unit 114 may draw room air samples from each of the plurality of rooms 102 perpetually during operation of the bulk supply fan 160 of the HVAC system 116. For example, the controller 120 of the air sampling system 100 may be configured to control the air flow controller 106 to direct a room air sample of a selected room 108 (e.g. room 12) to the quality sensor 140. The quality sensor 140 may then measure a condition or quality parameter of the selected room 108. Additionally, the air flow controller 106 may be configured to retrieve and purge room air samples 132 from each of the idle rooms 112 (e.g. rooms 11, 13, 14, and 21-24). By continuously drawing the room air samples 132 from each of the idle rooms 112 and the selected room 108, the air sampling system 100 may supply updated air samples to the air flow controller 106 without significant delay due to purging air samples. Accordingly, the air supplied to the at least one sensor 110 may only need to be purged of the air in the sensor supply line 124 when changing the selected room 108 among the plurality of rooms 102. In this way, the system may provide for economical monitoring of the air quality in each of the rooms 102 while maintaining a low cycle time for monitoring each of the rooms 102. Accordingly, the disclosure provides for a responsive monitoring system operable to quickly and effectively provide control information to a building management system 142 to ensure that room air quality is maintained throughout a building while limiting associated cost and maintenance fees.

Figure 4:
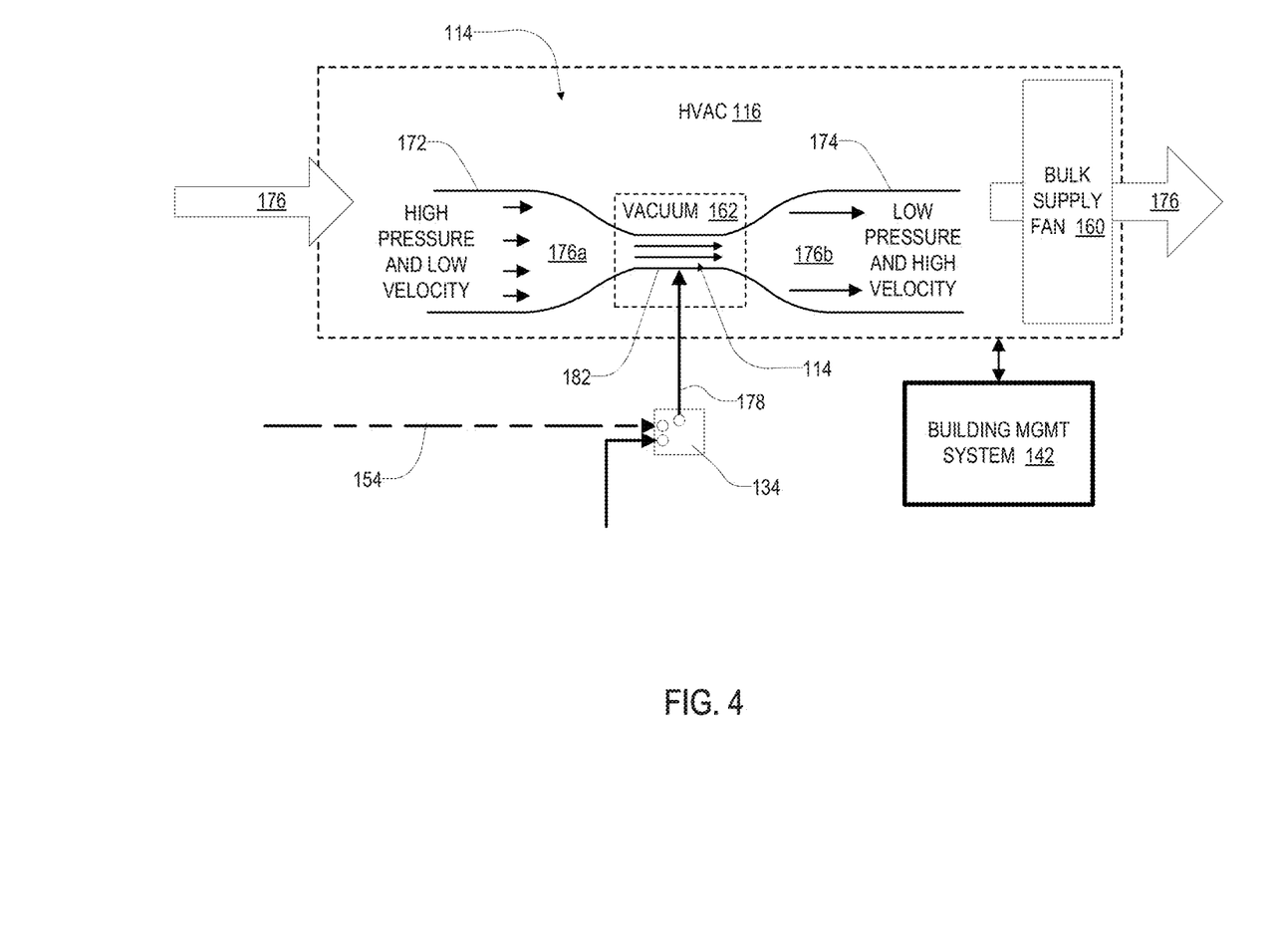
FIG. 4 is a detailed schematic diagram of the sample return unit of the air sampling system in accordance with the disclosure.

Referring to FIG. 4, a detailed schematic diagram sample return unit 114 of the air sampling device 104 is shown. As previously discussed, the sample return unit 114 may comprise the vacuum pump 162 configured to derive suction to draw the air samples from each of the plurality of rooms 102 to the air flow controller 106. The sample return unit 114 or air supply unit of the system 100 may be disposed in an air flow generated by an air supply unit or the bulk fan supply 160 of the HVAC system 116. The sample return unit 114 comprises an air inlet 172 and an air outlet 174. The air inlet 172 is configured to receive an inlet portion 176a of the air flow 176 and an outlet portion 176b released through the air outlet 174.

The inlet portion 176a of the air flow 176 may have an inlet pressure and an inlet velocity. The outlet portion 176b of the air flow 176 may have an outlet pressure and an outlet velocity. The sample return unit 114 may generate the suction of a suction line 178 by utilizing a pressure differential between the inlet pressure and the outlet pressure. For example, the pressure differential may be generated by the sample return unit 114 due to the Venturi effect causing the inlet pressure to be greater than the outlet pressure. Additionally, the Venturi effect may cause the inlet velocity to be lower than the outlet velocity. In this configuration, the difference between the inlet pressure and the outlet pressure created by the sample return unit 114 generates the suction that draws the room air samples via the vacuum pump 162 between the air inlet 172 and the air outlet 174.

The vacuum pump 162 comprises a vacuum section 182 disposed between the air inlet 172 and the air outlet 174. The vacuum section 182 forms a central cross-section perpendicular to the air flow 176. The central cross-section is smaller than an inlet cross-section of the air inlet 172 and an outlet cross section of the air outlet 174. In this configuration, the changes in the cross-sections among the air inlet 172, the vacuum section 182, and the air outlet 174 may result in vacuum pressure to be generated at the connection between the suction line 178 and the vacuum section 182. In this configuration, the sample return unit 114 may draw the air samples from each of the plurality of rooms 102 to the air flow controller 106. Accordingly, the air samples may be drawn from the plurality of rooms 102 throughout the operation of the air sampling system 100 in response to the activation of the air flow generated by the bulk fan supply 160 of the HVAC system 116.

It will be appreciated that embodiments of the disclosure described herein may be comprised of one or more conventional processors and unique stored program instructions that control one or more processors to implement, in conjunction with certain non-processor circuits, some, most, or all of the functions of an image sensor system and method thereof, as described herein. The non-processor circuits may include, but are not limited to, signal drivers, clock circuits, power source circuits, and/or user input devices. Alternatively, some or all functions could be implemented by a state machine that has no stored program instructions, or in one or more application specific integrated circuits (ASICs), in which each function or some combinations of the functions are implemented as custom logic. Of course, a combination of the two approaches could be used. Thus, the methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

It should be appreciated by those skilled in the art that the above described components may be combined in additional or alternative ways not explicitly described herein. Modifications of the various implementations of the disclosure will occur to those skilled in the art and to those who apply the teachings of the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

What is claimed is:

1. An air sampling system configured to detect an air quality metric for a plurality of volumetric regions, the system comprising:
an air sample unit configured to independently transfer air from the plurality of regions as a plurality of air samples;
an air flow controller configured to:
receive each of the plurality of air samples from the plurality of regions;
selectively direct a selected sample of the plurality of air samples to a sensor supply line and the remainder of the air samples to a sample purge line bypassing the sensor supply line; and
change the selected sample over time among the plurality of air samples such that the air quality metric is identified for the plurality of regions; and
at least one sensor in fluid communication with the sensor supply line and configured to measure the air quality metric of the selected sample and communicate the air quality metric to a controller, wherein the selected sample is drawn from the sensor supply line to the air sample unit and the remainder of the air samples are directed to the air sample unit throughout operation of the sampling system.

2. The air sampling system according to claim 1, further comprising the controller configured to:
output a control signal configured to direct the air flow controller to select an air sample of the plurality of air samples as the selected sample such that the selected sample is directed to the sensor supply line.

3. The air sampling system according to claim 2, wherein the controller is further configured to:
receive the sensor signal and communicate a ventilation signal to a building ventilation system in response to identifying the air quality metric identified from the sensor signal.

4. The air sampling system according to claim 3, wherein the ventilation signal identifies a specific region of the plurality of regions and the ventilation is configured to instruct the building ventilation system to provide at least one of hot air, cool air, and ventilation air to the specific region.

5. The air sampling system according to claim 1, wherein a first specific region corresponds to a first room and a second specific region corresponds to a second room.

6. The air sampling system according to claim 1, wherein the at least one sensor is configured to measure a carbon dioxide level of the selected sample.

7. The air sampling system according to claim 1, wherein the air sample unit corresponds to a Venturi Vacuum device.

8. The air sampling system according to claim 7, wherein the air sample return unit utilizes a pressure differential induced by an air flow of a building ventilation system to transfer the plurality of air samples from the plurality of regions.

9. An air sampling system configured to detect an air quality metric for a plurality of regions, the system comprising:
- an air sample unit disposed in an air flow generated by an air supply unit of an HVAC system, wherein the air sample unit is configured to generate a suction with energy derived from the air flow;
- an air flow controller configured to:
  - selectively transfer air from the plurality of regions via the suction as a plurality of air samples;
  - receive each of the plurality of air samples and selectively direct a selected sample of the plurality of air samples to a sensor supply line and the remainder of the plurality of air samples to a bypass line; and
  - change the selected sample over time among the plurality of air samples such that the air quality metric is identified for the plurality of regions; and
- at least one sensor in fluid communication with the air flow controller via the sensor supply line, wherein the at least one sensor is configured to measure the air quality metric of a selected sample of the plurality of air samples and communicate the air quality metric to a controller, wherein the selected sample and a remainder of the plurality of air samples are concurrently drawn to the air sample unit via the suction.

10. The sampling system according to claim 9, wherein the air sample return unit comprises an air inlet configured to receive an inlet portion of the air flow and an air outlet configured to release an outlet portion to the air flow.

11. The sampling system according to claim 10, wherein the inlet portion comprises an inlet pressure and an inlet velocity and the outlet portion comprises an outlet pressure and an outlet velocity.

12. The sampling system according to claim 11, wherein the inlet pressure is greater than the outlet pressure and the inlet velocity is lower than the outlet velocity.

13. The sampling system according to claim 11, wherein a difference between the inlet pressure and the outlet pressure generates the suction via a vacuum pump between the air inlet and the air outlet.

14. The sampling system according to claim 13, wherein the vacuum pump comprises a vacuum section of the air sample unit disposed between the air inlet and the air outlet.

15. The sampling system according to claim 14, wherein the vacuum section forms a central cross-section perpendicular to the airflow, and wherein the central cross-section is smaller than an inlet cross-section of the air inlet and an outlet cross section of the air outlet.

16. The sampling system according to claim 9, wherein the plurality of air samples is drawn from the plurality of regions throughout the operation of the air sampling system in response to the activation of the air flow.

17. A method for detecting air quality for a plurality of volumetric regions, the method comprising:
- receiving an air flow generated by an air supply unit;
- generating a suction in a suction line with energy derived from the air flow;
- drawing room air samples from a plurality of rooms with the suction;
- selectively directing at least one selected room air sample to a sensor device while directing a remainder of the room air samples to the suction line bypassing the at least one sensor;
- detecting an air quality metric of the at least one selected room air sample; and
- changing the at least one selected room air sample over time among the plurality of room samples such that the air quality metric is identified for the plurality of rooms.

18. The method according to claim 17, further comprising:
- communicating the air quality metric to a controller, wherein the controller is configured to control an HVAC system based on the air quality metric.

19. The method according to claim 17, wherein the air flow is generated by an air displacement device of the HVAC system.

* * * * *